United States Patent [19]

Van Der Puy et al.

[11] Patent Number: 5,395,997
[45] Date of Patent: Mar. 7, 1995

[54] PROCESS FOR THE PREPARATION OF HYDROFLUOROCARBONS HAVING 3 TO 7 CARBON ATOMS

[75] Inventors: Michael Van Der Puy, Cheektowage; G. V. Bindu Madhavan, Amherst; Timothy R. Demmin, Grand Island, all of N.Y.

[73] Assignee: AlliedSignal Inc., Morristownship, Morris County, N.J.

[21] Appl. No.: 99,677

[22] Filed: Jul. 29, 1993

[51] Int. Cl.$^6$ .................. C07C 17/08; C07C 17/28
[52] U.S. Cl. .................. 570/167; 570/166; 570/168; 570/172
[58] Field of Search ............. 570/165, 166, 167, 168, 570/169, 172

[56] References Cited

U.S. PATENT DOCUMENTS

| | | | |
|---|---|---|---|
| 2,439,299 | 4/1948 | Hovey et al. | 570/168 |
| 4,766,258 | 8/1988 | Komatsu et al. | 570/168 |

FOREIGN PATENT DOCUMENTS

| | | | |
|---|---|---|---|
| 431458 | 12/1991 | European Pat. Off. | |
| 50-106904 | 8/1975 | Japan | 570/168 |
| 8912616 | 12/1989 | WIPO | 570/168 |

OTHER PUBLICATIONS

Bloshchitsa, et al, "Reaction of Hydroxy-and Carbonyl Compounds with Sulfur Tetrafluoride", J. Org. Chem. USSR Eng. Translation, (Jul. 1985), vol. 21, 1414–20.
Hasek, et al, "Organic and Biological Chemistry, The Chemistry of Sulfur Tetrafluoride. II. The Fluorination of Organic Carbonyl Compounds", J. Am. Chem. Soc., (1960), 82, 543.
Kosolapoff, "Chemical Abstracts" 59:15175f, (1963).
"Chemical Abstracts" 63:483f, (1965), vol. 63, pp. 483–484.
"Chemical Abstracts" 68:48990d, 23—Aliphatic Compounds, (1968), vol. 68, p. 4727.
Maynard, "The Synthesis of Highly Fluorinated Compounds by Use of Potassium Fluoride in Polar Solvents", J. Org. Chem., (1963), vol. 28, p. 112.
Tarrant, et al, "Free Radical Additions Involving Fluorine Compounds. IV. The Addition of Dibromodifluoromethane to Some Fluoroolefins", J. Am. Chem. Soc., (1955), 77, p. 2783.
Henne et al, i "Fluorinated Derivatives of Propane and Propylene"1 , J. Am. Chem. Soc., (1946), 68, p. 496.
Belbachir et al, "Telomerization of Vinylidene Chloride I. Reactino With Carbon Tetrachloride by Redox Catalysis", Makromol. Chem., (1984), 185, 1583–1595.
Chem. Abstr., 115:207499h.

*Primary Examiner*—Alan Siegel
*Attorney, Agent, or Firm*—Karen A. Harding; Jay P. Friedenson

[57] ABSTRACT

The invention relates to a process for preparing hydrofluorocarbons of the formulas $CF_3(CH_2CF_2)_nF$ comprising reacting at least one reactant selected from $CCl_3(CH_2CCl_2)_nCl$, $CCl_3(CH_2CF_2)_nCl$ or $CCl_2[(CH_2CF_2)Cl]_2$, where n=1 to 3, with hydrogen fluoride at a temperature of from about 25° to about 200° C.

24 Claims, No Drawings

PROCESS FOR THE PREPARATION OF HYDROFLUOROCARBONS HAVING 3 TO 7 CARBON ATOMS

BACKGROUND OF THE INVENTION

FIELD OF INVENTION

This invention relates to the preparation of hydrofluorocarbons (HFCs). Specifically, it relates to the manufacture of a family of HFCs of the formula:

$$CF_3(CH_2CF_2)_nF \qquad\qquad I.$$

wherein n=1 to 3.

HFCs are of current interest due to their potential to replace ozone depleting CFCs and HCFCs which are used in a variety of applications such refrigerants, propellants, blowing agents, and solvents for degreasing, dewaxing, defluxing, and drying. The compound $CF_3CH_2CF_2CH_2CF_3(n=2)$ has physical properties (bp 69°–70° C.) that make it useful as a solvent, and has been (generically) claimed as such in European Patent Application 431 458 A1, published Dec. 6, 1991 (assigned to Daikin Industries) and has also been specifically mentioned as a solvent in U.S. application Ser. No. 746,273 filed Aug. 15, 1991 (assigned to AlliedSignal Inc.). The compound 1,1,1,3,3,3-Hexafluoropropane (n=1) has physical properties (bp −1 C.) which make it attractive a as blowing agent or propellant. It has been claimed as such in EP 381 986 A. The compound $CF_3(CH_2CF_2)_3F$ is a novel composition. Its bp of approximately 120° C. makes it a useful compound for e.g., dewaxing and other solvent applications.

There are several literature preparations disclosed for $CF_3CH_2CF_3$ but only one disclosed for $CF_3CH_2CF_2CH_2CF_3$. The latter involves the reaction of $SF_4$ with acetone dicarboxylic acid ($HOOCCH_2C(O)CH_2COOH$) as taught by Bloshchitsa et al., J. Org. Chem. USSR English Translation, 1985, 21, 1414.

Prior art preparations of $CF_3CH_2CF_3$ can be separated into those which involve precursors having no halogens other than fluorine and those which involve the fluorination of chlorinated or brominated precursors. The former type of processes include a) the reaction of $SF_4$ with propanedicarboxylic acid (J. Am. Chem. Soc., 1960, 82, 543), b) decarboxylation of $(CF_3)_2CHCOOH$ and its salts (Chem. Abstr., 59:15175f), c) from hexafluorothioacetone (Chem. Abstr., 63:483f), and d) the hydrolysis of appropriate precursors including $(CF_3)_2CHC(O)C_2F_5$ (Chem. Abstr., 92:180603e) and $(CF_3)_3CH$ (Chem. Abstr. 68:48990d). Processes which involve fluorination of precursors include a) fluorination of hexachloropropene, hexachloropropanes (but not $CCl_3CH_2CCl_3$), or heptachloropropanes with KF (J. Org. Chem., 1963, 28, 112), b) $SbF_3$ fluorination of $BrCF_2CH_2CF_2Br$ (J. Am. Chem. Soc., 1955, 77, 2783), c) $HgF_2$ fluorination of $CF_3CH_2CCl_3$ (J. Am. Chem. Soc., 1946, 68, 496), and d) fluorination of hexachloropropene with HF over a catalyst at 400–500 C. which gave $CF_3CHClCF_3$ as the main product and $CF_3CH_2CF_3$ also as a product (Chem. Abstr., 115:207499h).

Industry is continuing to search for alternatives to the preparations of $CF_3CH_2CF_3$ cited above, since they may be undesirable for one or more of the following reasons a) the cost of reactants is relatively expensive, b) yields are less than those desired for commercialization, or c) starting are not presently readily available. For example, one process disclosed in the literature for the preparation of $CF_3CH_2CF_2CH_2CF_3$ uses a relatively large quantity of $SF_4$. Because of the cost of $SF_4$, an alternative process is needed. Accordingly, it is the objective of this invention to provide an economical method for the preparation of telomer compounds of the formula $CF_3(CH_2CF_2)_{n=1-3}F$ using readily available raw materials.

SUMMARY OF THE INVENTION

One embodiment of the invention relates to a process for preparing hydrofluorocarbons of the formula:

$$CF_3(CH_2CF_2)_nF \qquad\qquad I.$$

wherein n=1 to 3 comprising reacting at least one reactant selected from $CCl_3(CH_2CCl_2)_nCl$, $CCl_3(CH_2CF_2)_nCl$ or $CCl_2[(CH_2CF_2)Cl]_2$ with hydrogen fluoride at a temperature of from about 25° to about 200° C. in the presence of a fluorination catalyst; wherein the HF is present in at least stoichiometric amounts per mole of reactant.

Another embodiment of this invention is a two-step process. In the first step, telomers are formed by reacting carbon tetrachloride with vinylidene chloride to give $CCl_3(CH_2CCl_2)_nCl$ or carbon tetrachloride with vinylidene fluoride to give $CCl_3(CH_2CF_2)_nCl$ or $CCl_2[(CH_2CF_2)Cl]_2$, where n is typically 1 to 3. The telomers (n=1–2) can optionally be separated into individual components by distillation. The second step of the process involves the fluorination of these telomers as described directly above using HF, preferably in the presence of a fluorination catalyst, such as an antimony(V) halide, at temperatures of about 25° to about 200° C.

DETAILED DESCRIPTION OF THE INVENTION

In observing compounds which are structurally related to the telomer reactants employed in this invention, we found that such related reactants such as $CFCl_2CH_2CCl_2CH_3$ underwent fluorination in the presence of HF without a catalyst to provide relatively high yields (i.e. greater than 50%). Unexpectedly, the fluorination of telomers of $CCl_3(CH_2CCl_2)_nCl$ resulted in relatively low yields. The yields were 13% or even as low as 2% or less for some of the telomers reactants (see examples 5, 6, & 9). Although one can prepare $CF_3(CH_2CF_2)_nF$ in the presence of HF alone, because of the low yields, industry desires a process which has a significantly higher yield of the products. We discovered that the relatively low yields of the fluorination process can be enhanced significantly when the fluorination catalyst is conducted in the presence of a fluorination catalyst. A fluorination catalyst as used herein is any inorganic metal catalyst used for the substitution of fluorine for chlorine on hydrochlorofluorocarbons (compounds containing carbon, chlorine, fluorine and hydrogen), hydrochlorocarbons (compounds containing carbon, chlorine and hydrogen) and chlorofluorocarbons (compounds containing carbon, chlorine and fluorine) or mixtures thereof. Unexpectedly, the yields of the desired fluorinated telomer are greater than 50%, and as high as 80%+).

The fluorination catalysts employed are metal halides. Preferably, they are selected from halides of Sn, Ti, Ta and Sb. Illustrative of such catalysts are metal (IV) halides and metal (V) halides. More preferred catalysts are metal halides wherein the halogen is chlorine, fluorine or a combination thereof. Additional catalysts are selected from $SnCl_4$, $TiCl_4$, $SbF_5$, $SbCl_5$ or $SbF_mCl_{5-m}$ wherein m ranges from 1 to 4. Both $SnCl_4$ and $TiCl_4$ exhibited marked improvement in the yield of fluorinated products relative to HF alone, but the most preferred catalysts are Sb(V) hal ides, such as $SbF_5$, $SbCl_5$ and $SbF_mCl_{5-m}$, with m=1 to 4. These catalysts exhibited superior yields, which can allow for lower operating temperatures and provide shorter reaction times than without the catalysts or with less efficient catalyst.

Apparatus for conducting these fluorinations are coventional devices. The apparatus consists of a direct drive stirring, monel autoclave equipped with a condenser for cooling. By-product HCl is vented periodically to maintain a desired operating pressure, e.g. of about 400 psig. Lower operating pressures (e.g. 100–200 psig) may also be used for larger reactors which may have lower pressure ratings. During the venting of HCl, some HF and lower boiling products (e.g., $CF_3CH_2CF_3$, bp $-1°$ C.) may be vented simultaneously, particularly at lower operating pressures. Organic starting material and HF may be added under pressure to supply additional reactants for a continuous process.

When Sb(V) halides are used as the catalyst, it.is advantageous to also co-feed chlorine in an amount (e.g. at least about 1 to 20 mole percent of chlorine) sufficient to maintain the antimony salts in the +5 oxidation state, (the latter being more active than antimony (III) halides).

Useful temperatures will depend on the amount and activity of the catalyst used. The temperature should be selected to effect a sufficient yield of the desired product. Useful temperatures range from about 25° to about 225° C., the preferred temperatures being about 75° to about 150° C. when these catalysts are employed. With Sb(V) halides, temperatures in the 50–125 C. range are useful, 75°–100° C. being preferred. Temperatures ranging from 125 to 150 C. are best for the less active catalysts, such as $SnCl_4$ and $TiCl_4$, which are similar to each other in activity.

The amount of HF supplied to the reactor should be at least stoichiometric, i.e., at least about 6 moles HF per mole $CCl_3CH_2CCl_3$ or at least about 8 moles HF per mole $CCl_3CH_2CCl_2CH_2CCl_3$. Generally, more HF than stoichiometric is employed so that HF is essentially a solvent for the fluorination reaction. Excessive amounts of HF limit the output of the product for a batch process. Thus 1 to about 10 times the stoichiometric amount is preferred. We have employed quantities of HF corresponding to 3 to 5 times the stoichiometric amounts with good results.

Reaction times are dependent on several factors including catalyst concentration, the type of catalyst, and the temperature. For a batch process, the progress of the reaction can be conveniently monitored by the increase in pressure due to the formation of by-product HCl. Typical reaction times range from a few hours to about one day.

The amount of catalyst used can vary widely. The amount can depend on the catalyst employed, reactants and other process variables. Although relatively low catalyst concentrations are effective (e.g. less than 0.05 mole per mole organic added), substantial quantities (0.1 to 0.5 mole catalyst per mole of organic) may be desirable in order to enhance the reaction rate and consequently improve product output. The more preferred amount of catalyst used is 0.1 to 0.25 mole of catalyst per mole of organic.

Although any method may be used for forming the chlorine-containing reactants which are to be fluorinated in the above-discussed processreactants, preferably, these reactants are formed by the reaction of $CCl_4$ with a vinylidene chloride or vinylidene fluoride (hereafter both are referred to as the vinylidene reactant). The telomerization of vinylidene reactant, preferably, vinylidene chloride can be initiated by several means, but initiation with metal salts, particularly of copper, has distinct advantages for the process of this invention. The copper salts are believed to initiate the reaction by first reacting with $CCl_4$ to produce a trichloromethyl radical which then combines with vinylidene chloride, initiating the telomerization (see for example, Assher and Vofsi, J. Chem. Soc., 1961, 2261 for a discussion of the mechanism). The copper salts also terminate the telomerization by chlorine atom transfer to the growing radical chain. Thus, the chain lengths are shortened considerably, compared to e.g. peroxide initiated telomerizations. For the reactions of interest here, the telomers of 3 to 7 carbons are obtained in sufficient yield for potential commercialization (hereafter a sufficient yield of reactant or product is at least 24%, and at least 50% is preferred. Some control of the telomer distribution is possible by controlling the reaction conditions, notably $CCl_4$ to vinylidene chloride ratios and the type of copper salt used (see for example Belbachir et al., Makromol. Chem. 1984, 185, 1583–1595). Thus, it is possible to obtain $CCl_3CH_2CCl_3$ with very little higher molecular weight telomers. It is considerably more difficult to obtain only one of the higher molecular weight telomers (5-carbon and higher) starting from $CCl_4$ and vinylidene chloride. However, if only the 5-carbon material is desired, a mixture of primarily 3-carbon and 5-carbon telomers can be obtained (see Example 1), and the 3-carbon material recycled to give the 5-carbon telomer by reaction with vinylidene chloride (see Example 2). An analogous procedure can be used to prepare the 7-carbon telomer from the 5-carbon telomer.

A variety of catalysts have been used in telomerization processes. To a large degree, many of these telomerization catalysts, including mixtures thereof, can often be equivalent, and the choice of catalyst depends on cost, availability, and solubility in the reaction medium. For the telomerization reaction of this invention, it was discovered that salts of copper and iron are preferred. Overall, for the reaction of interest here, the more preferred catalysts are cuprous chloride, cupric chloride, or mixtures of the two or cuprous iodide. The amount of catalysts used in the telomerization reaction is at least about 0.1 mmol, and preferably, about 0.1 to about 50 mmol, per mole of saturated halogenated hydrocarbon (e.g., $CCl_4$ or $CCl_3CH_2CCl_3$) used. At very low concentrations, the reaction rate may be unacceptably slow, and very high catalyst concentrations may be wasteful due to the fact that the solubility limit may have been reached at even lower catalyst to $CCl_4$ ratios. Consequently, the more preferred amount of catalyst is about 1 to 20 mmol, per mole of saturated halogenated hydrocarbon.

It is also noted that a co-catalyst can be used in the telomerization process. Amines may be employed as co-catalysts, preferably in concentration of 1 to 10 moles per mole of metal catalyst (i.e. copper salt). Such amine co-catalysts include alkanol amines, alkyl amines and aromatic amines, for example ethanolamine, butyl amine, propyl amine, benzylamine, pyridine and the like.

The ratio of $CCl_4$ to vinylidene reactant will substantially alter the degree of polymerization (average value of n). Thus, for example, if the desired product has only one more —$CH_2CCl_2$— unit than the starting material, the ratio of $CCl_4$ (or $CCl_3CH_2CCl_3$) to vinylidene chloride should be relatively high (at least about 2, and preferably, about 2 to 5), so that higher molecular weight telomers are minimized. If the desired product has two or more —$CH_2CCl_2$— units than the starting material (e.g. $CCl_3(CH_2CCl_2)_2Cl$ from $CCl_4$), smaller ratios of $CCl_4$ to vinylidene chloride (about 0.3 to 1) should be used. The same rationale is used for a system employing vinylidene fluoride.

Useful temperatures for the telomerization reaction range from about 25° to about 225° C., preferably 80° to about 170° C., so that, depending on reactant concentrations and catalyst activity, convenient reaction times will vary from a few hours to about one day. More preferred temperatures are in the 125° to 140° C. range.

Finally a variety of solvents can be used. Any solvent in which the reactants form the desired product in sufficient yield can be used. Illustrative of such are acetonitrile, dimethylsulfoxide, dimethylformamide, tetrahydrofuran isopropanol, and tertiary butanol. We prefer acetonitrile due to its low cost, stability, easy recovery via distillation, and ability to dissolve sufficient amounts of inorganic catalyst salts. Primarily for the latter consideration, the amount of solvent is preferably from about one fourth to two thirds of the total volume, and more preferably one third to one half of the total volume. Otherwise, the amount of dissolved catalyst may be relatively low, or the output of product per run will be adversely affected due to a dilution effect.

Having described the invention in detail and by reference to the preferred embodiments thereof, it will be apparent that modifications and variations are possible without departing from the scope of the invention defined in the appended claims and illustrative examples.

EXAMPLES

Example 1

Preparation of $CCl_3CH_2CCl_3$ and $CCl_3(CH_2CCl_2)_2Cl$ from $CCl_4$

A 750 mL, direct drive stirring autoclave was charged with 75 mL acetonitrile, 75 mL $CCl_4$, 40.4 g vinylidene chloride, and 0.1 g of catalyst made up by mixing equal weights of cuprous chloride and cuptic chloride dihydrate. The mixture was heated to 130°–134° C. for 18 h, cooled, and poured into 200 mL water. The organic phase was separated, and the aqueous layer extracted with 50 mL $CH_2Cl_2$. The combined organic layers were then dried ($Na_2SO_4$) and concentrated by rotary evaporation to provide 82.7 g of crude product. Distillation at 1 mm Hg gave 68.5 g $CCl_3CH_2CCl_3$ (bp 47°–50° C.), 12.1 g $CCl_3CH_2CCl_2CH_2CCl_3$ (bp 109°–114° C.), and 5.5 g pot residue which contained primarily the above material and $CCl_3(CH_2CCl_2)_3Cl$. The total yield of 3- and 5-carbon materials accounts for 82.5% of the vinylidene chloride added.

Example 2

Preparation of $CCL_3(CH_2CCl_2)_2Cl$ from $CCl_3CH_2CCl_3$

In a manner similar to that described in Example 1, 101 g of $CCl_3CH_2CCl_3$, 75 mL $CH_3CN$, 42.3 g vinylidene chloride, and 0.75 g of the same catalyst were heated to 130°–136° C. for 24 h. Distillation of the crude material, obtained after workup, gave 50.3 g recovered $CCl_3CH_2CCl_3$ and 48.5 g of a mixture of primarily $CCl_3(CH_2CCl_2)_2Cl$ and $CCl_3(CH_2CCl_2)_3Cl$. Distillation of the latter gave 39.4 g of 98% pure $CCl_3(CH_2CCl_2)_2Cl$ (57% yield based on unrecovered $CCl_3CH_2CCl_3$).

Example 3

Fluorination of a mixture of essentially pure $CCl_3CH_2CCl_3$ with HF and $SbF_5$ as catalyst A 600 mL, magnetically stirred, monel autoclave fitted with a condenser (maintained at $-10°$ C.), was evacuated, cooled to about $-40°$ C., and charged with 7.6 g (0.035 mole) $SbF_5$, followed by 64 g (0.255 mole) $CCl_3CH_2CCl_3$, and 100 g (5 mole) HF. The temperature was increased to 125° C. and maintained at that temperature for a total of 18 h. During the heating period, pressure in excess of 400 psig was periodically vented to an aqueous KOH scrubber which was attached to two $-78°$ C. cold traps. At the end of the heating period, the remainder of the autoclave contents were slowly vented. The cold traps contained 33.4 g colorless liquid which consisted of 97.9% $CF_3CH_2CF_3$ and 0.5% $CF_3CH_2CF_2Cl$ for a yield of 85%.

Example 4

Fluorination of $CCl_3CH_2CCl_3$ with HF and $TiCl_4$ as catalyst

In the apparatus described in Example 2, 64.4 g $CCl_3CH_2CCl_3$, 102.5 g HF and 6.9 g (0.036 mole) $TiCl_4$ heated to 120° C. for 22 hours. The cold traps contained 36.1 g material which by GC analysis, contained 13.1% $CF_3CH_2CF_3$ and 69% $CF_3CH_2CF_2Cl$. No olefinic materials were observed.

Example 5

Fluorination of $CCl_3CH_2CCl_3$ with HF and $SnCl_4$ as catalyst

In the manner and apparatus described in Example 3, 63.5 g $CCL_3CH_2CCl_3$, 101.4 g HF, and 13.5 g (0.052) $SnCl_4$ were heated to 125° C. for 23.5 h. The cold trap contained 41.5 g material, which by GC analysis contained 13.4% $CF_3CH_2CF_3$, 66.3% $CF_3CH_2CF_2Cl$, and 20.3% $CF_3CH_2CFCl_2$.

Example 6

Fluorination of $CCl_3CH_2CCl_3$ with HF at 100° C.

In the apparatus used in Example 2, 64 g (0.25 mole) $CCl_3CH_2CCl_3$ and 81 g HF (4.05 mole) were heated to 100° C. for 22 h. Although $CF_3CH_2CF_3$ was identified as one of the minor products (less than 2% yield), the major volatile products, identified by GC-MS analysis, included partially fluorinated propanes, e.g., $C_3H_2Cl_2F_4$ and $C_3H_2Cl_4F_2$, along with some olefinic by-products. This Example shows that HF alone can be used to prepare $CF_3CH_2CF_3$, but the results are inferior to those involving the use of a catalyst ($SbF_5$ or $TiCl_4$ or $SnCl_4$).

Example 7

Fluorination of $CCl_3CH_2CC_3$ with HF at 145° C.

In the same manner as Example 5, 64 g $CCl_3CH_2CCl_3$ and 76 g HF were heated to 145° C. for 23 h. The cold trap contained 30 g crude product which was comprised of a mixture of chlorofluoropropanes as observed in Example 5. 1,1,1,3,3,3-Hexafluoropropane was present to the extent of about one percent.

Example 8

Fluorination of essentially pure $CCl_3(CH_2CCl_2)_2$ with HF using $SbF_5$ as catalyst In the apparatus described in Example 3, $SbF_5$ (8.5 g, 0.039 mole), 71.7 g (0.206 mole) $CCl_3(CH_2CCl_2)_2$, and 96.6 g HF (4.83 mole) were heated to 125° C. for a total of 18 h. Pressures in excess of 450 psig were vented to the scrubber and cold traps as in Example 3. At the end of the heating period, the temperature was increased to 150° C. and the remainder of the autoclave contents were vented. From the KOH scrubber there was obtained 24.5 g of 98.6% pure $CF_3CH_2CF_2CH_2CF_3$, while the cold traps contained 3.7 g of 96% pure $CF_3CH_2CF_2CH_2CF_3$ for a total yield of 28.2 g (68% yield).

Example 9

Fluorination of $CCl_3(CH_2CCl_2)_2Cl$ with HF

A mixture of 39.4 g (0.11 mole) $CCl_3(CH_2CCl_2)_2Cl$ and 74.7 g (3.74 mole) HF was heated in an autoclave to 145° C. for 3 h. A total of 18.3 g organic material was recovered, which contained only a trace of $CF_3CH_2CF_2CH_2CF_3$ as determined by GC-MS analysis. The crude product was a complex mixture.

Example 10

Fluorination of a mixture of chlorocarbons, $CCl_3(CH_2CCl_2)nCl$ (n=1 to 3), with HF and an Sb(V) chlorofluoride catalyst The catalyst used in this example was prepared by heating 11.7 g $SbCl_5$ (0.039 mole) and 19.5 g (0.98 mole) HF to 70° C. for 1 hour. The mixture was then cooled to −40° C., and HCl bled off. Organic chlorocarbon (65 g) used in this example was (by GC analysis) comprised of 11.5% $CCL_3CH_2CCl_3$, 74.5% $CCl_3CH_2CCl_2CH_2CCl_3$, and 14% $CCl_3(CH_2Cl_2)_3Cl$. The mixture was then heated to 125° C. An operating pressure of 400-500 psig was used. After the specified reaction time, the contents were vented to the usual scrubber and cold traps. After warming the traps to room temperature, a total of 22.2 g volatile material was obtained. Of this, about 18.6 g was $CF_3CH_2CF_2CH_2CF_3$, and 2.5 g was $CF_3(CH_2CF_2)_3F$. Distillation gave 99.4% pure $CF_3CH_2CF_2CH_2CF_3$, bp 69-70 C. (1H NMR (CDCl3): symmetrical multiplet centered at δ2.9; 19F NMR: 63.2 (6 F) and 93.0 (2F) ppm upfield from CFCl3), and 94% pure $CF_3CH_2CF_2CH_2CF_2CH_2CF_3$, bp 115°-122° C. (1H NMR (CDCl3): unsymmetrical multiplet at δ2.4-3.3; 19F NMR: 62.8 (6F) and 92.5 (4F) ppm upfield from CFCl3).

This example demonstrates the successful fluorination of the mixture of chlorocarbons, thus showing that purified materials need not be employed, and also demonstrates the first preparation of $CF_3(CH_2CF_2)_3F$.

Example 11

In the addition reactions involving $CCl_4$, vinylidene fluoride may be substituted for vinylidene chloride to make compounds of the formula $CCl_3(CH_2CF_2)nCl$ and/or $CCl_2(CH_2CF_2)nCl$. Vinylidene fluoride is less reactive than vinylidene chloride and somewhat higher (20°-80° C. higher) temperature and/or longer reaction times are required.

Fluorination of these adducts proceeds under conditions similiar to those used in the fluorination of $CCl_3(CH_2CCl_2)nCl$ compounds. In this case, however, the stoichiometric amount of HF required is reduced, e.g. 4 moles HF for the fluorination of 1 mole $CCl_3CH_2CF_2Cl$ to $CF_3CH_2CF_3$.

An autoclave was charged with 75 mL $CCl_4$, 75 mL acetonitrile, 1 g cuprous iodide, and 3 mL pyridine. The autoclave was closed, evacuated briefly to remove air, and charged with 24.3 g vinylidene fluoride. The contents were then heated with stirring to 150° C. for 24 hours. The cooled contents were poured into 200 mL water and the phases separated. The aqueous phase was extracted with 25 mL $CCl_4$, and the combined organic phases were washed with saturated NaCl solution and dried ($Na_2SO_4$). Distillation gave 14.3 g (17% yield) of $CCl_3CH_2CF_2Cl$, boiling point 60°-62° C. at 65 mm Hg (purity 98%). 1H NMR (CDCl3: δ3.85 (t, J=12 Hz); 19F NMR: 51.8 ppm upfield from internal CFCl3(t, J=12 Hz).

Example 12

Preparation of $CCl_3(CH_2CCl_2)nCl$ using CuI/pyridine as the catalyst system.

In Examples 1 and 2, an autoclave was used for the preparation of $CCl_3(CH_2CCl_2)nCl$ since, at the reaction temperatures of about 130° C., the pressure is about 120 psig at the beginning of the reaction. By using the catalyst system consisting of cuprous iodide and pyridine, however, the reaction may be conducted at much lower reaction temperatures and at atmospheric pressure.

A 500-mL flask was purged with nitrogen and charged with 2 g CuI, 280 mL carbon tetrachloride, 40 mL acetonitrile, and 50 mL vinylidene chloride. The mixture was stirred and heated to reflux (65° C.). Pyridine (6.5 mL) was then added, and reflux was continued for 21 hours. The reaction mixture was cooled, filtered, washed with 100 mL concentrated HCl, and then washed with a mixture of 50 mL saturated aqueous NaCl and 50 mL of 10% aqueous NaOH solution. Distillation gave 55.2 g (35% yield) of $CCl_3CH_2CCl_3$ and 18.7 g $CCl_3CH_2CCl_2CH_2CCl_3$ (17 % yield).

Comparative Example 1

Fluorination of $FCCl_2CH_2CCl_2CH_3$ with HF

This comparative example shows that the fluorination of a structurally similar material ($FCCl_2CH_2CCl_2CH3$) proceeded in good yield under conditions (HF without catalyst) where both $CCl_3CH_2CCl_3$ and $CCl_3(CH_2CCl_2)_2Cl$ were fluorinated in very poor yield (Examples 5, 6, and 9). An autoclave was charged with 150 g of 75% pure $FCCl_2CH_2CCl_2CH_2$(the other identified components were $CCl_3CH_2CFClCH_3$ (4%), $C_4H_5Cl_3F_2$ (15.5%), $C_2H_2Cl_4$ (2.5%), $C_2H_3Cl_3$ (2.7%)), and 150 g HF. The reaction mixture was heated to 150°-160° C. for 6-7 hours, during which time the pressure was maintained at 450-500 psig by periodically venting excess pressure (the vented gases were passed through a KOH scrubber, which was connected in sequence to −15° C. and −78° C. cold traps). The remainder of the contents were then vented. The cold traps contained 60 g of crude product which was 85-90% pure $CF_3CH_2CF_2CH_3$. The combined crude product from 4 such runs was distilled to give 159 g of 97% pure $CF_3CH_2CF_2CH_3$ (50% yield).

What is claimed is:

1. A process for preparing hydrofluorocarbons of the formula:

$$CF_3(CH_2CF_2)_nF \qquad \text{I.}$$

wherein n=1 to 3 comprising reacting at least one reactant selected from $CCl_3(CH_2CCl_2)_nCl$, $CCl_3(CH_2CF_2)_nCl$ and $CCl_2[CH_2CF_2)Cl]_2$ with hydrogen fluoride at a temperature of from about 25° to about 200° C. in the presence of at least one fluorination catalyst selected from the group consisting of halides of Sn, Ti, Ta and Sb; wherein the HF is present in at least stoichiometric amounts per mole of reactant.

2. The process of claim 1 wherein said reactant is $CCl_3(CH_2CCl_2)_nCl$.

3. The process of claim 1 wherein said reactant is $CCl_3(CH_2CF_2)_nCl$.

4. The process of claim 1 wherein said reactant is $CCl_2[(CH_2CF_2)Cl]_2$.

5. The process of claim 1 wherein said catalyst is a Sn, Ti, Ta or Sb (V) halide.

6. The process of claim 1 wherein the halide in said fluorination catalyst is selected from chlorine, fluorine or a combination thereof.

7. The process of claim 1 wherein the catalyst is selected from $SnCl_4$, $TiCl_4$, $SbF_5$, $SbCl_5$ or $SbF_mCl_{5-m}$ wherein m ranges from 1 to 4.

8. The process of claim 1 wherein said reaction is conducted at from about 25° to about 225° C.

9. The process of claim 1 wherein said reaction is conducted at from about 40° to about 175° C.

10. The process of claim 1 wherein said reaction is conducted at from about 50° to about 150° C.

11. The process of claim 1 wherein said process further comprises preparing $CCl_3(CH_2CCl_2)_nCl$, $CCl_3(CH_2CF_2)_nCl$ or $CCl_2[(CH_2CF_2)Cl]_2$ by reacting $CCl_4$ with vinylidene chloride or vinylidene fluoride.

12. The process of claim 11 wherein said process is conducted in the presence of metal catalyst.

13. The process of claim 11 wherein catalyst is a metal salt of copper or iron.

14. The process of claim 12 wherein the catalyst is cuprous chloride, cupric chloride, or a mixture thereof or cuprous iodide.

15. The process of claim 12 wherein the amount of catalysts used is at least about 0.1 mmol per mole $CCl_4$.

16. The process of claim 12 wherein said amount of catalyst ranges from about 0.1 to 50 mmol per mole of $CCl_4$.

17. The process of claim 12 wherein said amount of catalyst ranges from about 1 to about 20 mmol per mole of $CCl_4$.

18. The process of claim 12 wherein said process is conducted in the presence of a co-catalyst.

19. The process of claim 12 wherein the co-catalyst is an amine.

20. The process of claim 12 wherein said process of preparing $CCl_3(CH_2CCl_2)_nCl$, $CCl_3(CH_2CF_2)_nCl$ or $CCl_2[(CH_2CF_2)_mCl]_2$ is conducted at temperature of from about 40° to about 225° C.

21. The process of claim 5 wherein chlorine is added in an amount sufficient to substantially maintain the catalyst salt in a +5 oxidation state.

22. The process of claim 11 wherein said process of preparing $CCl_3(CH_2CCl_2)_nCl$, $CCl_3(CH_2CF_2)_nCl$ or $CCl_2[(CH_2CF_2)_mCl]_2$ is conducted in an organic solvent.

23. The process of claim 22 wherein said organic solvent is selected from acetonitrile, dimethylsulfoxide, dimethylformamide tetrahydrofuran, isopropanol, and tertiary butanol.

24. The process of claim 19 wherein said catalyst is cuprous iodide and said amine co-catalyst is pyridine.

* * * * *